(12) United States Patent
Sungu et al.

(10) Patent No.: US 11,413,160 B2
(45) Date of Patent: Aug. 16, 2022

(54) HIP JOINT ENDOPROSTHESIS SYSTEM

(71) Applicant: Aesculap AG, Tuttlingen (DE)

(72) Inventors: Mevluet Sungu, Schaffhausen (CH); Anil Varsani, Tuttlingen/Moehringen (DE)

(73) Assignee: Aesculap AG, Tuttlingen (DE)

( * ) Notice: Subject to any disclaimer, the term of this patent is extended or adjusted under 35 U.S.C. 154(b) by 468 days.

(21) Appl. No.: 16/517,766

(22) Filed: Jul. 22, 2019

(65) Prior Publication Data
US 2019/0336307 A1 Nov. 7, 2019

Related U.S. Application Data

(63) Continuation of application No. PCT/EP2018/051501, filed on Jan. 23, 2018.

(30) Foreign Application Priority Data

Jan. 23, 2017 (DE) .................... 10 2017 101 191.9

(51) Int. Cl.
*A61F 2/46* (2006.01)
*A61F 2/36* (2006.01)
*A61F 2/30* (2006.01)

(52) U.S. Cl.
CPC .......... *A61F 2/4607* (2013.01); *A61F 2/3662* (2013.01); *A61F 2/4603* (2013.01); *A61F 2002/30474* (2013.01); *A61F 2002/4619* (2013.01); *A61F 2002/4628* (2013.01); *A61F 2002/4681* (2013.01)

(58) Field of Classification Search
CPC ........... A61F 2/4607; A61F 2002/4619; A61B 17/8872; A61B 17/92
See application file for complete search history.

(56) References Cited

U.S. PATENT DOCUMENTS

| | | | | |
|---|---|---|---|---|
| 3,818,514 A | * | 6/1974 | Clark | A61F 2/4607 606/86 R |
| 3,857,389 A | * | 12/1974 | Amstutz | A61F 2/4607 606/86 R |
| 4,601,289 A | * | 7/1986 | Chiarizzio | A61B 17/1659 606/85 |
| 4,686,971 A | * | 8/1987 | Harris | A61F 2/4607 606/99 |

(Continued)

FOREIGN PATENT DOCUMENTS

| | | |
|---|---|---|
| DE | 9212846 | 1/1993 |
| DE | 4439309 | 3/1996 |

(Continued)

*Primary Examiner* — David W Bates
(74) *Attorney, Agent, or Firm* — Lipsitz & McAllister, LLC (57) ABSTRACT

The invention relates to a hip joint endoprosthesis system, comprising a medical instrument for extracting an implanted prosthesis stem of a hip joint endoprosthesis from a femur bone of a patient, which medical instrument has a coupling body with a coupling recess for accommodating a coupling cone protruding from the prosthesis stem, wherein the coupling body comprises a coupling base body and a coupling insert which is accommodated in a coupling insert receptacle of the coupling base body and defines the coupling recess.

30 Claims, 6 Drawing Sheets

(56) References Cited

U.S. PATENT DOCUMENTS

| | | | | |
|---|---|---|---|---|
| 4,993,410 A | * | 2/1991 | Kimsey | A61F 2/4607 |
| | | | | 606/100 |
| 5,674,225 A | * | 10/1997 | Muller | A61B 17/1659 |
| | | | | 606/100 |
| 5,743,910 A | * | 4/1998 | Bays | A61F 2/4607 |
| | | | | 606/99 |
| 6,322,564 B1 | * | 11/2001 | Surma | A61F 2/4607 |
| | | | | 606/89 |
| 2010/0298943 A1 | * | 11/2010 | Berry | A61F 2/30724 |
| | | | | 623/18.11 |
| 2016/0287396 A1 | * | 10/2016 | Huff | A61F 2/4637 |
| 2016/0338751 A1 | * | 11/2016 | Kellar | A61F 2/4607 |
| 2018/0028249 A1 | * | 2/2018 | Jaumard | A61F 2/4607 |

FOREIGN PATENT DOCUMENTS

| | | |
|---|---|---|
| DE | 202005001040 | 5/2005 |
| DE | 102008064518 | 7/2010 |
| EP | 0207873 | 1/1987 |
| EP | 0940127 | 9/1999 |
| FR | 2770128 | 4/1999 |
| WO | 9013271 | 11/1990 |
| WO | 2016187305 | 11/2016 |

\* cited by examiner

HIP JOINT ENDOPROSTHESIS SYSTEM

CROSS-REFERENCE TO RELATED APPLICATIONS

This application is a continuation of international application number PCT/EP2018/051501 filed on Jan. 23, 2018 and claims the benefit of German application number 10 2017 101 191.9 filed on Jan. 23, 2017, which are incorporated herein by reference in their entirety and for all purposes.

FIELD OF THE INVENTION

The present invention relates to hip joint endoprosthesis systems generally, and more specifically to a hip joint endoprosthesis system, comprising a medical instrument for extracting an implanted prosthesis stem of a hip joint endoprosthesis from a femur bone of a patient, which medical instrument has a coupling body with a coupling recess for accommodating a coupling cone projecting from the prosthesis stem.

BACKGROUND OF THE INVENTION

For the treatment of damaged hip joints, the latter have been replaced by hip joint endoprostheses for many years. A prosthesis stem is hereby inserted into a cavity of the femur bone prepared therefor. Prosthesis stems are known that have a projecting coupling cone which, for example, is coupleable to a neck extension or joint ball. A further component of the hip joint endoprosthesis is the joint socket which is fixed in the pelvis bone of the patient. The acetabulum may optionally accommodate a joint insert which forms a sliding pairing with the joint ball that is as wear-resistant as possible.

If, for example, in the course of an operation for implanting the hip joint endoprosthesis, a prosthesis stem that is too large or too small is inserted into the prepared bone cavity, the same must be removed. For this purpose, medical instruments are used that have a coupling body which is coupleable to the coupling cone of the prosthesis stem. One problem here is in particular that the coupling cone may be damaged when cooperating with the coupling body of the medical instrument. This is absolutely undesirable because a damaged coupling cone no longer enables a secure connection with a neck piece or a joint ball. The connection between the coupling cone and the neck piece or the joint ball hereby occur by self-locking. For this purpose, surfaces which are optimally adapted to each other are necessary. Scratches and raised portions on the coupling cone prevent a secure self-locking connection.

SUMMARY OF THE INVENTION

In a first aspect of the invention, a hip joint endoprosthesis system comprises a medical instrument for extracting an implanted prosthesis stem of a hip joint endoprosthesis from a femur bone of a patient. Said medical instrument has a coupling body with a coupling recess for accommodating a coupling cone protruding from the prosthesis stem. Said coupling body comprises a coupling base body and a coupling insert which is accommodated in a coupling insert receptacle of the coupling base body and defines the coupling recess.

BRIEF DESCRIPTION OF THE DRAWING FIGURES

The foregoing summary and the following description may be better understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a hip joint endoprosthesis system, comprising a medical instrument for extracting an implanted prosthesis stem of a hip joint endoprosthesis from a femur bone of a patient, which medical instrument has a coupling body with a coupling recess for accommodating a coupling cone protruding from the prosthesis stem, wherein the coupling body comprises a coupling base body and a coupling insert which is accommodated in a coupling insert receptacle of the coupling base body and defines the coupling recess.

The further development, proposed in accordance with the invention, of a medical instrument of the kind described at the outset makes it possible in particular to delimit the coupling recess with a material which is softer than the coupling cone of the prosthesis stem. Damage to the coupling cone may thus be prevented in a simple and secure manner. The at least two-part configuration of the coupling body by a coupling base body and a coupling insert also makes it possible to optionally form the coupling insert and the coupling base body of different materials. Thus the coupling insert may be formed in particular of a material with which the risk of damage to the coupling cone is minimized. The coupling base body, however, may be of sufficiently stable configuration in order to transmit forces to be applied for the extraction of the prosthesis stem and to introduce said forces into the coupling cone.

The coupling base body is favorably formed of a harder material than the coupling insert. Damage to the coupling cone of the prosthesis stem by the coupling body may thus be minimized if the coupling cone is only able to come into contact and cooperate with the coupling insert. For example, the coupling cone may be formed of an implant steel or in particular of titanium or a titanium alloy. The coupling insert is then preferably formed of a material which is softer than the material of which the coupling cone is formed.

In order to ensure a sufficient stability of the medical instrument, it is advantageous if the coupling base body is formed of a metal. In particular, the coupling base body may be formed of an instrument steel, for example a cobalt chrome alloy.

The hip joint endoprosthesis system may be configured in a simple and inexpensive manner if the coupling insert is formed of a plastic. In particular, the plastic may be polyetheretherketone (PEEK) and/or polypropylene (PP) and/or polyphenylene sulfone (PPSU). The stated plastics may be simply and safely sterilized and are sufficiently soft in order to prevent a damaging of the coupling cone, but are sufficiently dimensionally stable in order to be able to transmit forces required for the extraction of the prosthesis stem from the femur bone to the prosthesis stem.

It is favorable if the medical instrument comprises at least one first coupling element for coupling to an instrument handle. This makes it possible in particular to configure the coupling body in the form of an adapter, also called an extraction adapter, which may be coupled to an instrument handle. It is thus possible in particular to provide a plurality of coupling bodies having coupling recesses of different sizes and different shapes, but only one instrument handle. A surgeon may then, for example, select the suitable coupling body, bring it into engagement with the coupling cone of the prosthesis stem, and then couple it to the instrument handle in order to extract the prosthesis stem. Modular hip joint endoprosthesis systems may thus be formed, which require a minimal number of parts in order to extract a multiplicity of different prosthesis stems.

The coupling base body may be formed in a simple manner if the first coupling element is configured in the form of a coupling projection. The latter may, for example, be accommodated by a corresponding coupling element receptacle on the instrument handle.

The medical instrument preferably comprises an instrument handle. The instrument handle may in particular be formed as one piece with the coupling base body. Said instrument handle may, however, as described, also be temporarily coupleable to the coupling base body. For example, the instrument handle may be configured in the form of a rasp handle. In particular, the rasp handle may be configured as is described in DE 10 2008 064518 A1. The instrument handle may in particular be coupled to a rasp body to form a surgical rasp. The cavity in the femur bone may be prepared with the rasp before the insertion of the prosthesis stem of the hip joint endoprosthesis. When the bone cavity is prepared in the desired manner, the rasp handle may be separated from the rasp body. For example, the coupling base body may then be coupled to the rasp handle by bringing the rasp handle into engagement with the first coupling element. As a result of this modular design, the number of instruments required for an implantation of a hip joint endoprosthesis may be further minimized.

It is advantageous if the instrument handle comprises a striking body with a striking face, and if the striking body is arranged or formed on a proximal end of the instrument handle or forms the proximal end of the instrument handle. When the instrument handle is coupled to the coupling body, by acting upon the striking face of the striking body, for example with a hammer, force impacts may be transmitted from the instrument handle via the coupling body to the prosthesis stem coupled to the medical instrument in order to release said prosthesis stem from the femoral shaft or to loosen a connection between the prosthesis stem and the femur of the patient.

The instrument handle may be connected to the coupling body in a simple manner if the instrument handle comprises at least one second coupling element for bringing into engagement in a force- and/or positive-locking manner with the at least one first coupling element in a coupling position. In particular, the first and second coupling elements are formed correspondingly to each other and are adapted to each other for an optimal coupling.

The at least one second coupling element is preferably configured in the form of a coupling element receptacle for accommodating the at least one first coupling element. Providing a coupling element receptacle is advantageous in particular if the first coupling element is configured in the form of a coupling projection corresponding to the coupling element receptacle.

It is advantageous in particular for minimally invasive surgical interventions if the at least one second coupling element is arranged or formed on a distal end of the instrument handle or forms the distal end of the instrument handle. The instrument handle may thus be brought into engagement with the coupling body in a simple and secure manner.

The coupling recess is preferably configured to accommodate the coupling cone in a force- and/or positive-locking manner. Thus a stable connection between the coupling body and the coupling cone of the prosthesis stem may be formed, an extraction of the prosthesis stem from the femur bone thereby being made easier.

In accordance with a further preferred embodiment of the invention, provision may be made for the coupling recess to have a lateral insertion opening for inserting the coupling cone into the coupling recess in an insertion direction which runs transversely, in particular perpendicularly, to a longitudinal axis defined by the coupling cone. In particular, the longitudinal axis may be defined by the axis of symmetry of the coupling cone. The medical instrument may thus be guided with the coupling body next to the coupling cone and then be pushed in the insertion direction over the coupling cone in order to accommodate the same in the coupling recess.

Furthermore, it is advantageous if the coupling recess has a lower insertion opening which is open in a direction transverse, in particular perpendicular, to the insertion direction. The lower insertion opening makes it possible in particular that the prosthesis stem does not have to be separated from the coupling cone in order to extract the prosthesis stem. The lower insertion opening may in particular be passed through by a connecting region on the prosthesis stem when the medical instrument is in engagement with the coupling cone of the prosthesis stem. The connecting region connects the coupling cone to the actual shaft of the prosthesis stem. In particular, said shaft, the connection region, and the coupling cone may be formed as one piece to form the prosthesis stem.

It is further advantageous if the coupling base body surrounds the coupling insert in such a way that the lateral insertion opening and the lower insertion opening are freely accessible when the coupling insert is inserted into the coupling insert receptacle. The coupling cone may thus be inserted into the coupling recess, wherein it is only able to come into contact with the coupling insert, but not with the coupling base body. A damaging of the coupling cone by the coupling base body may thus be avoided.

The coupling insert preferably defines edges or transition regions delimiting the lateral insertion opening and/or the lower insertion opening. It is thus ensured, in particular, that, when inserting the coupling cone into the coupling recess, the coupling cone is only able to come into contact with the coupling insert, the risk of damage to the coupling cone thereby being minimized.

In order to achieve a particularly good transmission of force between the medical instrument and the prosthesis stem, it is advantageous if the coupling recess has an inner contour which has the form of an inner cone at least in sections. In particular, said inner cone may be formed correspondingly to the coupling cone in order to at least partially achieve an areal abutment of the coupling cone against the coupling recess.

The coupling body may be coupled to the coupling cone in a simple manner if the inner cone defines a longitudinal cone axis which passes through the lower insertion opening.

In particular, coupling cones tapering away from the prosthesis stem may be brought into engagement with the coupling body if a cross section of the inner cone increases in the direction toward the lower insertion opening.

In order to be able to exert, in particular, tensile or compressive forces on the prosthesis stem with the medical instrument, it is advantageous if a cross-sectional narrowing is formed between the inner cone and the lower insertion opening. The cross-sectional narrowing may in particular engage into the transition region between the coupling cone and the shaft of the prosthesis stem, which may be configured in the form of a constriction. As a result, in particular the cross-sectional narrowing on the coupling body may be inserted laterally into the constriction on the prosthesis stem. The cross-sectional narrowing may be configured, e.g., in the form of an annular projection pointing in the direction toward the longitudinal cone axis, which annular projection is not completely closed in itself.

It is advantageous if the coupling insert receptacle has a lateral coupling insert receptacle opening and a lower coupling insert receptacle opening. The coupling insert may thus be inserted through the lateral coupling insert receptacle opening into the coupling insert receptacle. The lower coupling insert receptacle opening makes it possible, in particular, for the lower insertion opening of the coupling insert to remain freely accessible.

The lateral coupling insert receptacle opening is preferably configured for the insertion of the coupling insert into the coupling insert receptacle. The coupling insert and the coupling base body may thus be brought into engagement with each other in a simple and secure manner.

In order to be able to transmit, in particular tensile forces with the medical instrument to the prosthesis stem, it is favorable if the coupling insert receptacle has an undercut which is formed by a reduction of a free cross section of the coupling insert receptacle in the direction toward the lower coupling insert receptacle opening. Thus, in particular forces in axial direction, i.e. in particular in parallel to the longitudinal cone axis, may be transmitted from the coupling base body to the coupling insert without the coupling insert being able to release from the coupling base body.

The coupling insert is favorably held in the coupling insert receptacle in a force- and/or positive-locking manner. This makes it possible in particular to separate the coupling insert from the coupling base body, for example for cleaning the medical instrument.

In accordance with a further preferred embodiment of the invention, provision may be made for the medical instrument to comprise a connecting device for connecting the coupling insert and the coupling base body in a connecting position in a force- and/or positive-locking manner. In particular a defined connection between the coupling insert and the coupling base body may be ensured with the connecting device.

The hip joint endoprosthesis system may be configured in a simple and inexpensive manner if the connecting device is configured in the form of a latching or snapping connecting device.

The connecting device may be configured in a simple manner if it comprises first and second connecting elements which are formed on the coupling insert on the one hand and on the coupling base body on the other hand, and if the first and second connecting elements are in engagement in a force- and/or positive-locking manner in the connecting position.

It is advantageous if the first connecting element is configured in the form of a connecting element recess and if the second connecting element is configured in the form of a connecting projection. In particular, the first and second connecting elements are formed correspondingly to each other. They may also selectively be formed on the coupling base body and on the coupling insert.

It is favorable if the first and/or the second connecting elements extend in parallel or substantially in parallel to the lateral coupling insert receptacle opening and/or to the lateral insertion opening. This may be understood in particular in that the lateral insertion opening defines an insertion opening plane and the connecting elements extend in parallel thereto. This has the advantage in particular that, as a result of the connecting elements in engagement with each other, the coupling insert is not able to be moved out of the coupling insert receptacle without additional extraction forces. In particular, the connecting elements may thus extend transversely to the insertion direction and prevent a relative movement between the coupling insert and the coupling base body.

The medical instrument may be configured in a simple manner if the connecting element formed on the coupling body in the coupling insert receptacle is arranged or formed pointing in the direction toward the lower coupling insert receptacle opening. For example, said connecting element may be configured as a connecting projection or as a connecting element receptacle, for example as a rib or groove.

In order to be able to use the medical instrument, in particular in the case of minimally invasive surgeries, it is advantageous if the first coupling element is arranged on the coupling base body in such a way that it points counter to or substantially counter to the lower coupling insert receptacle opening. For example, the first coupling element is configured in the form of a coupling projection which protrudes from the coupling base body and points in a direction counter to the direction, pointing in which the lower coupling insert receptacle opening is open.

In accordance with a further preferred embodiment of the invention, provision may be made for the hip joint endoprosthesis system to comprise a release instrument for releasing the coupling insert from the coupling insert receptacle of the coupling base body. The release element makes it possible in particular to separate the coupling insert and the coupling base body from each other in order to clean and sterilize them.

It is favorable if the release instrument comprises a release member, if the coupling base body comprises a release member opening, and if the release member has a length which is greater than a thickness of the coupling base body in the region of the release member opening. This configuration makes it possible in particular that, by inserting the release member into the release member opening, the release member is able to project into the coupling insert receptacle in such a way that a compressive force can be exerted on the coupling insert, preferably in a direction parallel to the insertion direction, whereby the coupling insert may be pushed or pressed, respectively, out of the coupling insert receptacle. In particular, the forces required for releasing the connecting device, i.e. for bringing the mutually engaged first and second connecting elements out of engagement, may thus be transmitted to the coupling insert.

The coupling insert may be released from the coupling base body in a particularly simple manner if the release member opening is arranged or formed opposite the lateral coupling insert receptacle opening. The coupling insert may thus be pressed directly out of the coupling insert receptacle through the lateral coupling insert receptacle opening.

The release element may be configured in a simple manner if the release member is configured in the form of a release pin projecting from the release element.

The forces acting between the engaged connecting elements of the connecting device may be overcome particularly easily for releasing the coupling insert and the coupling base body from each other if the release member is provided with an external thread and if the release member opening is provided with an internal thread corresponding to the external thread. The release member may thus be screwed into the release member opening, a release force thereby being able to be transmitted to the coupling insert in a very metered manner.

In accordance with a further preferred embodiment of the invention, provision may be made for the hip joint endoprosthesis system to comprise a prosthesis stem of a hip joint endoprosthesis, which prosthesis stem has a projecting coupling cone. In particular, the hip joint endoprosthesis system may comprise a plurality of different prosthesis stems of that kind. The hip joint endoprosthesis system may comprise corresponding coupling bodies suitable for each coupling cone of the prosthesis stems, such that a modular hip joint endoprosthesis system may be formed.

Figure 1:
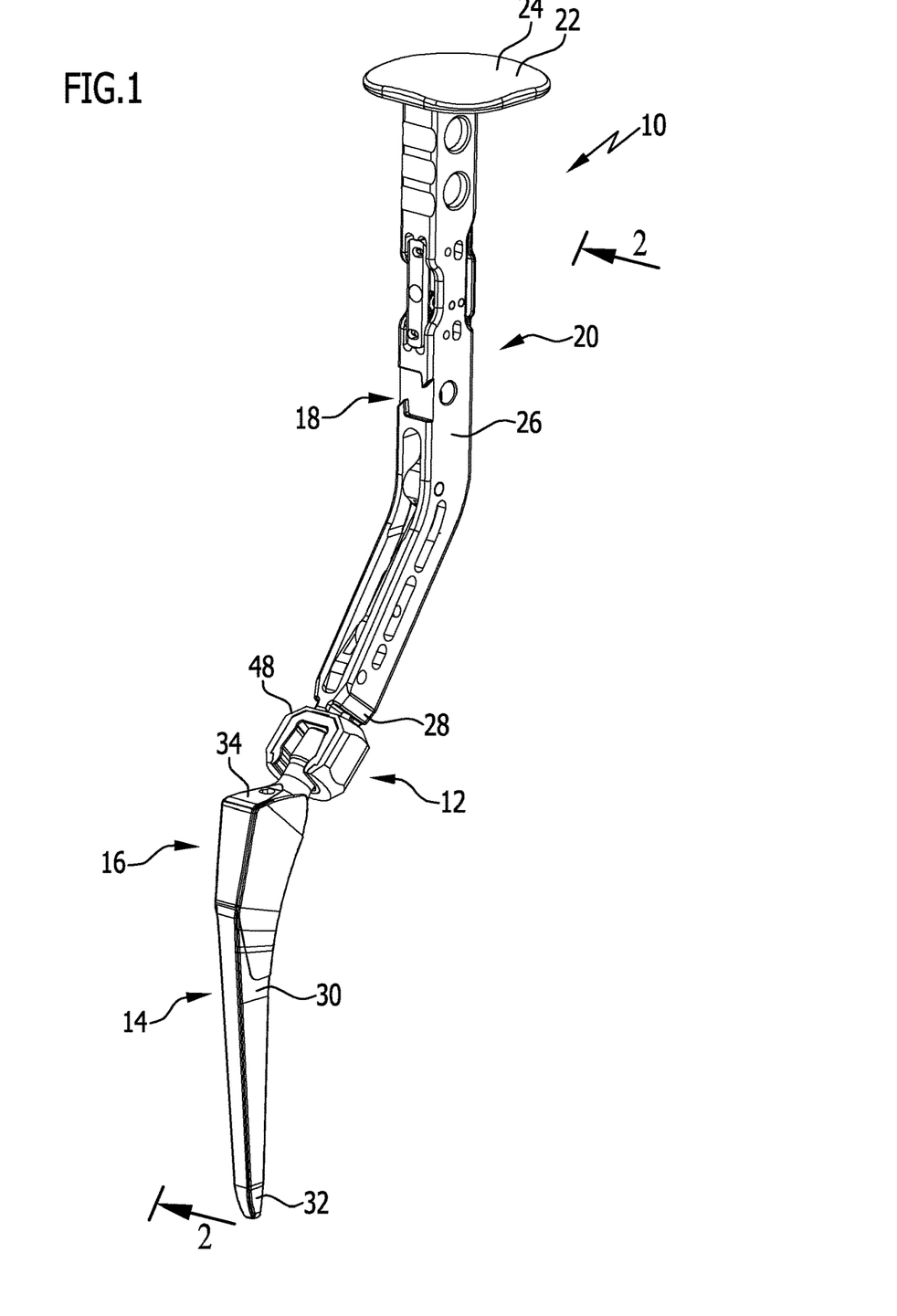
FIG. 1: shows a perspective total view of a hip joint endoprosthesis system in accordance with the invention.

A first embodiment of a hip joint endoprosthesis system designated as a whole with the reference numeral 10 is schematically depicted in FIG. 1. It comprises a medical instrument 12 for extracting an implanted prosthesis stem 14 of a hip joint endoprosthesis 16 from a femur bone of a patient.

Optionally, the hip joint endoprosthesis system 10 further comprises the prosthesis stem 14 and further optionally an instrument handle 18. The latter may be configured in particular in the form of a rasp handle 20, as it is described, e.g., in DE 10 2008 064 518 A1.

The instrument handle 18 has at its proximal end a striking body 22 with a striking face 24 which points in a proximal direction and is weakly convexly curved pointing away from the instrument handle 18. It thus forms, as is depicted for example in FIG. 1, the proximal end of the instrument handle 18.

The instrument handle 18 has an elongate, bent instrument body 26 which extends from the striking body 22 to a distal end of the instrument handle 28.

The prosthesis stem 14 comprises an elongated shaft body 30 which tapers in cross section toward a distal end 32.

A coupling cone 38, tilted in relation to an end face 36 of the shaft body 30, projects from a proximal end 34 of the latter. The coupling cone 38 is configured in the form of a truncated cone which tapers in cross section in the direction toward a circular end face 40 pointing away from the shaft body 30.

A short neck section 44 connects to a distal end 42 of the coupling cone 38, which neck section 44 is reduced in cross section at the distal end 42 of the coupling cone 38 and thus forms a constriction between the coupling cone 38 and the shaft body 30.

The coupling cone 38 serves in the hip joint endoprosthesis 16 to connect to a joint ball not depicted in the Figures, which has a receiving cone corresponding to the coupling cone 38, such that the prosthesis stem 14 and joint ball may be connected to each other by self-locking. Optionally, if necessary, the coupling cone 38 may also be coupled to an extension section, which is not depicted, in the described manner as with the joint ball, wherein the extension section in turn may be coupled to the joint ball.

If the prosthesis stem 14 is inserted into a cavity prepared therefor of the femur bone of the patient, but does not fit as the surgeon desires, then he/she must again extract the prosthesis stem 14 from the femur bone. The instrument 12 serves this purpose. Said instrument 12 is configured in the form of a two-part extraction adapter 46 and serves as a coupling body 48 with a coupling recess 50 for accommodating the coupling cone.

The coupling body 48 comprises a coupling base body 52 with a coupling insert receptacle 54 in which a coupling insert 56 is accommodated in a force- and/or positive-locking manner. The coupling recess 50 is formed on the coupling insert 56.

The coupling base body 52 is formed of a harder material than the coupling insert 56. For example, the coupling base body 52 may be formed of a metal, in particular of an instrument steel.

The coupling insert 56 is preferably formed of a material that is softer than the material of which the prosthesis stem 14 is formed, in particular the coupling cone 38 thereof. Thus the risk may be minimized that the coupling cone 38 may be damaged when being received in the coupling recess 50 of the extraction adapter 46. The coupling insert 56 is preferably formed of a plastic. For example, said plastic may be polyetheretherketone (PEEK), polypropylene (PP), and/or polyphenylene sulfone (PPSU). PEEK here has in particular the most suitable mechanical material reference values, in particular tensile and compressive strength, hardness, and modulus of elasticity.

In order to be able to couple the instrument 12 to the instrument handle 18, a first coupling element 60 is arranged or formed on the coupling body 48 on an end face 58 pointing in the proximal direction. Said coupling element 60 may in particular, as is schematically depicted in the Figures, be configured in the form of a coupling projection 62 which defines a coupling projection longitudinal axis 64 that runs transversely to the end face 58, in particular perpendicularly thereto. A recess 66 which defines an undercut is formed laterally on the coupling projection 62.

Figure 2:
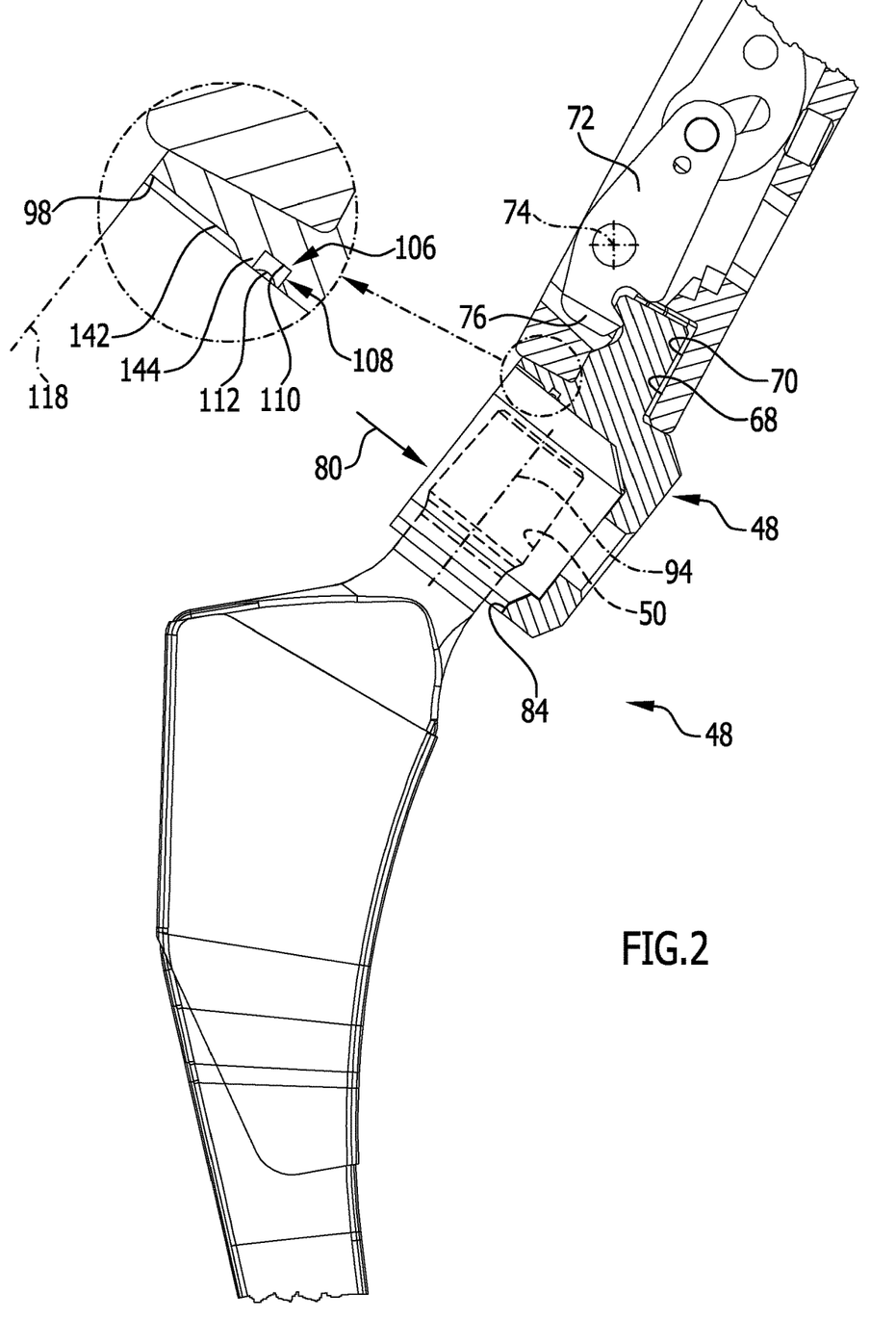
FIG. 2: shows a partially cut view of the arrangement from FIG. 1 along line 2-2.
Figure 3:
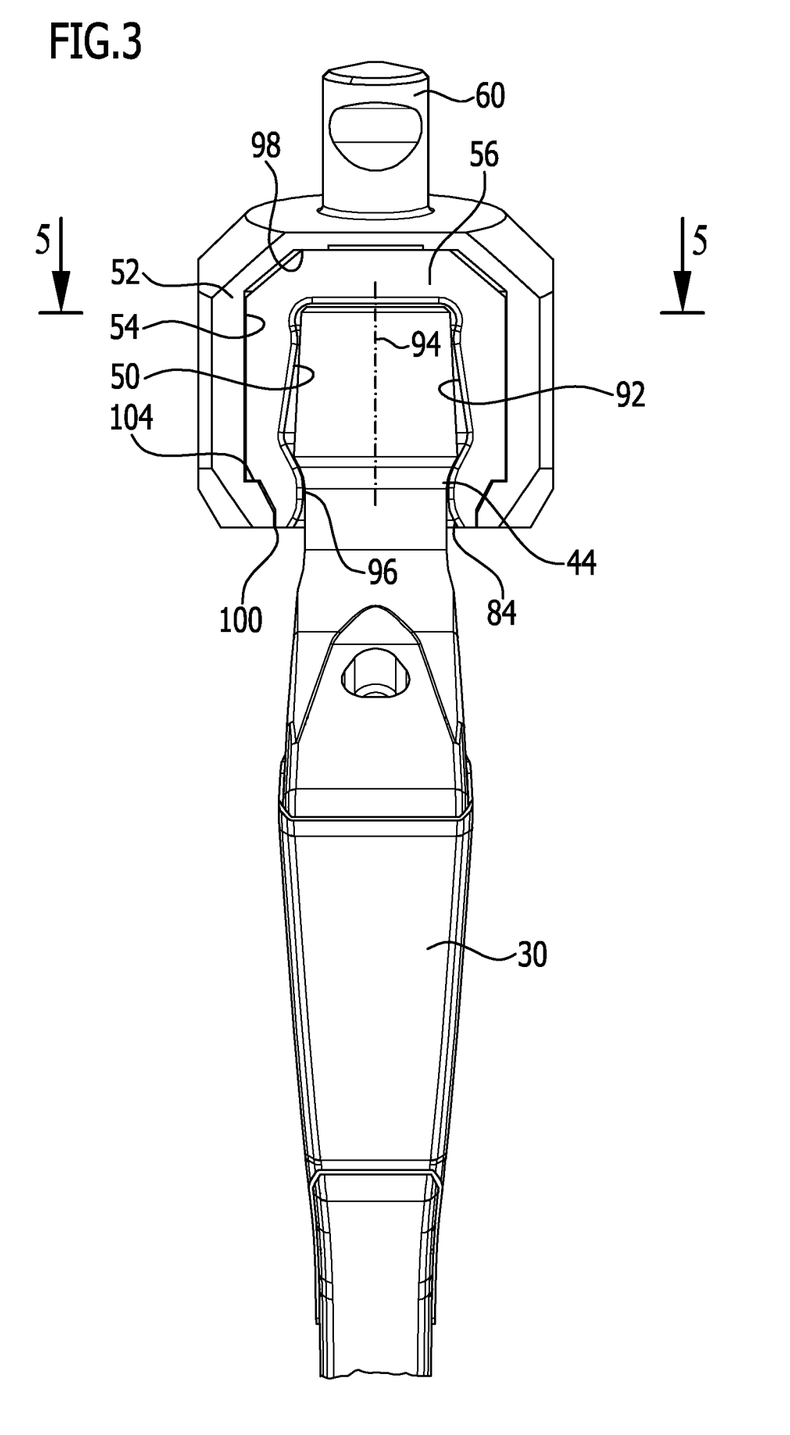
FIG. 3: shows a side view of a coupling body coupled to a prosthesis stem.
Figure 4:
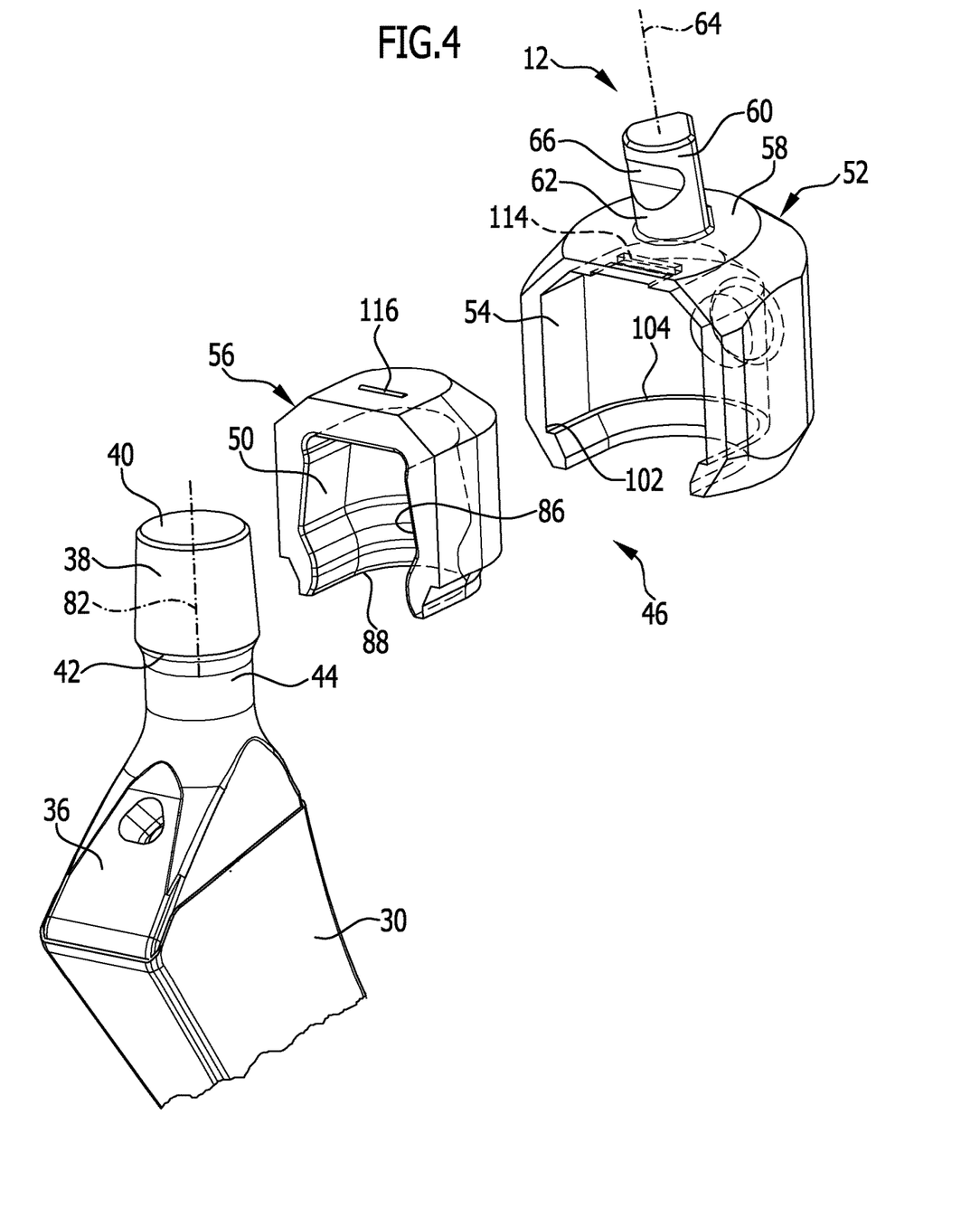
FIG. 4: shows an exploded depiction of the prosthesis stem, of the coupling base body, and of the coupling insert.
Figure 5:
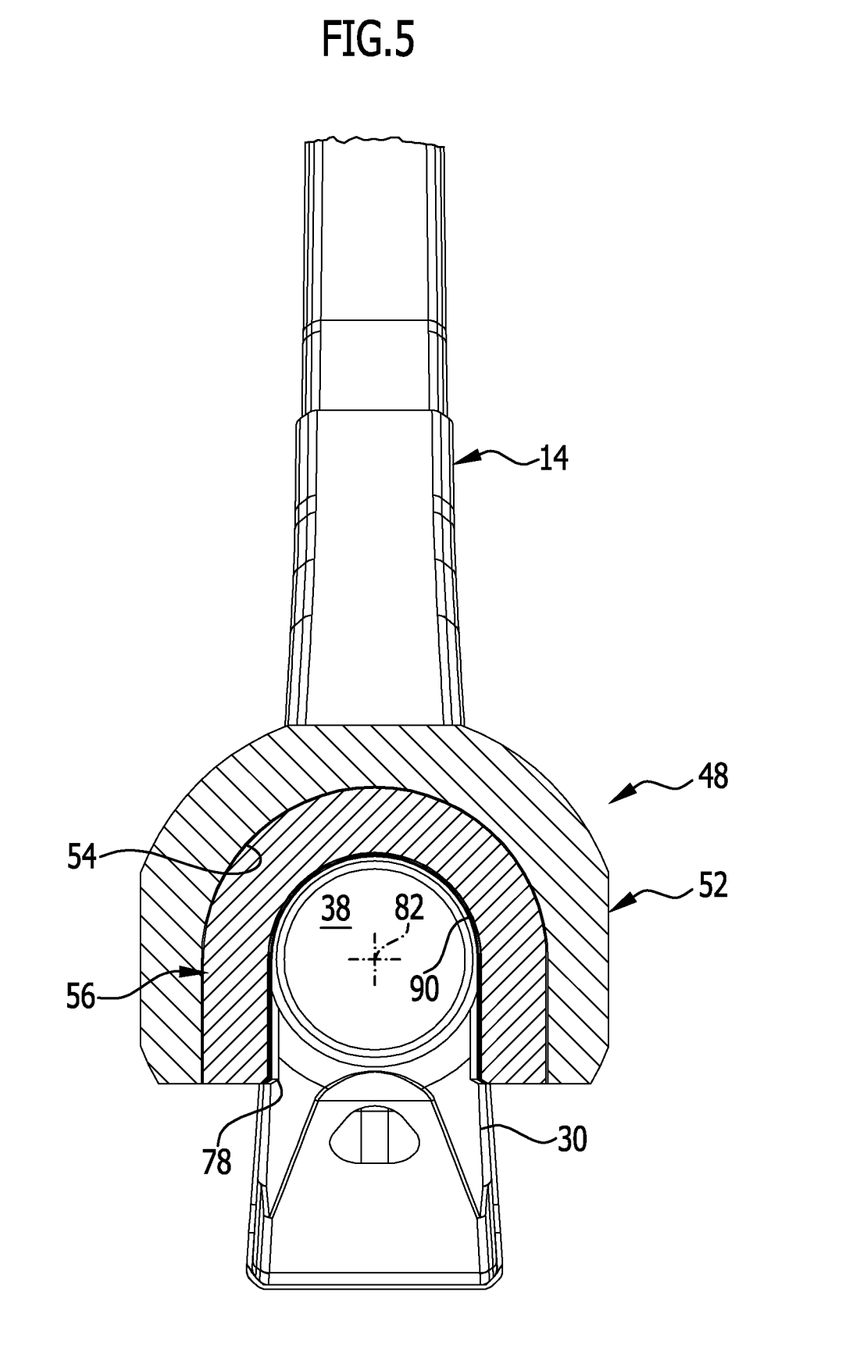
FIG. 5: shows a sectional view along line 5-5 in FIG. 3.
Figure 6:
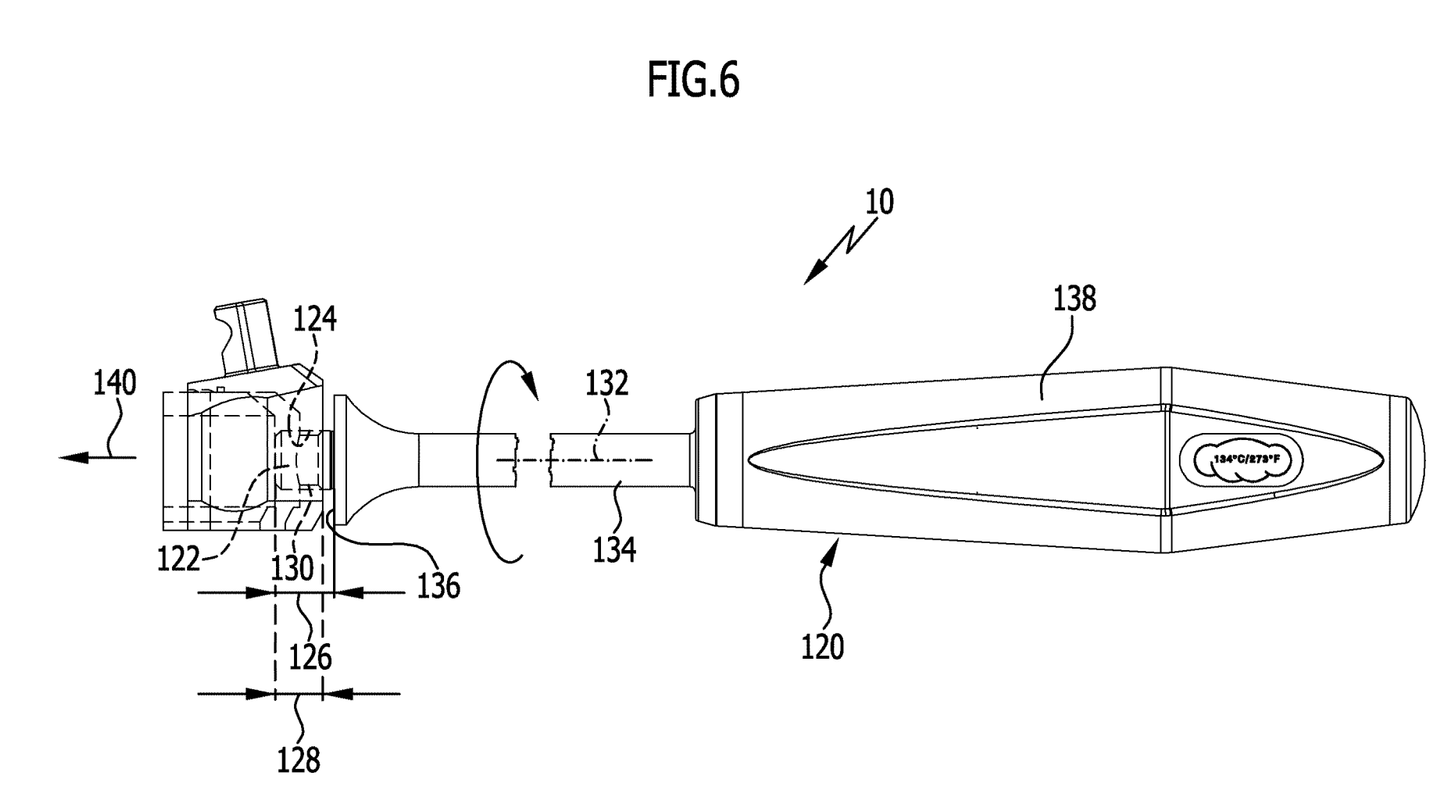
FIG. 6: shows a partially broken side view of the coupling body when releasing the coupling insert out of the coupling base body with a release element.

A second coupling element 68 corresponding to the first coupling element 60 is formed on the instrument handle 18 for bringing into engagement in a force- and/or positive-locking manner with the first coupling element 60 in a coupling position, which is depicted for example in FIGS. 1 to 3. The second coupling element 68 is configured in the form of a coupling element receptacle 70 for accommodating the first coupling element 60. The coupling element receptacle 70 is formed correspondingly to the coupling projection 62 and accommodates the latter in a positive-locking or substantially positive-locking manner.

Serving for securing the extraction adapter 46 to the instrument handle 18 is a pivotable securing member 72 which is mounted on the instrument handle 18 so as to be pivotable about a pivot axis 74 running transversely to the coupling projection longitudinal axis 64. An end of the securing member 72 on the distal side is configured in the form of a locking nose 76 which, in a locking position, is pivoted into the recess 66, as is depicted for example in FIG. 2, and, in a release position in which the instrument handle 18 may be removed from the extraction adapter 46, is pivoted out.

The securing member 72 is coupled to a corresponding pivoting mechanism on the instrument handle 18 in order to pivot it about the pivot axis 74 for connecting to or for releasing from the first coupling element 60. In particular, the pivoting mechanism may be configured as described in DE 10 2008 064 518 A1.

The second coupling element 68 is arranged on the distal end 28 of the instrument handle 18 or forms the end 28, respectively.

The coupling recess 50 is configured to accommodate the coupling cone 38 in a force- and/or positive-locking manner. It has a lateral insertion opening 78 for pushing the coupling cone 38 into the coupling recess 50 in an insertion direction that is indicated schematically in FIG. 2 by the arrow 80. The insertion direction 80 runs transversely, in particular perpendicularly, to a longitudinal axis 82 defined by the coupling cone 38.

The coupling recess 50 further has a lower insertion opening 84 which is open in a direction transverse, in particular perpendicular, to the insertion opening 80.

The coupling base body 52 is configured in a shell-like manner or in the form of a shell and surrounds the coupling insert 56 in such a way that the lateral insertion opening 78 and the lower insertion opening 84 are freely accessible when the coupling insert 56 is accommodated in the coupling insert receptacle 54. This configuration is easy to see, in particular in FIGS. 1 to 3.

The coupling insert 56 defines the lateral insertion opening 78 as well as edges 86 and 88, respectively, defining the lower insertion opening 84.

The coupling recess 50 has an inner contour 90 which at least has the form of an inner cone 92 at least in sections.

The inner cone 92 defines a longitudinal cone axis 94 which passes through the lower insertion opening 84. The inner cone 92 further has a cross section which increases in the direction toward the lower insertion opening 84.

The coupling recess 50 is further configured in such a way that a cross-sectional narrowing 96 is formed between the inner cone 92 and the lower insertion opening 84. When the prosthesis stem 14 is coupled to the extraction adapter 46, the cross-sectional narrowing 96, which forms, as it were, an annular projection convexly curved in the direction toward the longitudinal cone axis 94, engages into the neck section 44 between the coupling cone 38 and the shaft body 30.

The coupling insert receptacle 54 has a lateral coupling insert receptacle opening 98 and a lower coupling insert receptacle opening 100. The coupling insert 56 may be pushed through the correspondingly formed lateral coupling insert receptacle opening 98 into the coupling insert receptacle 54, also in the insertion direction 80.

Serving to secure the coupling insert 56 in the coupling insert receptacle in axial direction, i.e. parallel to the longitudinal cone axis 94, is an undercut 102 which is delimited by an annular face 104 that points in the proximal direction and is not closed in itself. The undercut 102 is formed by a reduction of a free cross section of the coupling insert receptacle 54 in the direction toward the lower coupling insert receptacle opening 100.

An outer contour of the coupling insert 56 is substantially matched to an inner contour of the coupling insert receptacle 54, such that the coupling insert 56 is held in the coupling insert receptacle 54 in a force- and/or positive-locking manner.

A connecting device 106 is provided on the medical instrument 12 for securing the coupling insert 56 in the coupling insert receptacle 54 against a movement counter to the insertion direction 80, such that the coupling insert 56 and the coupling base body 52 are connected to each other in a connecting position, depicted for example in FIG. 2, and in a force- and/or positive-locking manner.

The connecting device 106 may be configured in particular in the form of a latching or snapping connecting device 108.

The connecting device 106 comprises a first connecting element 110 and a second connecting element 112 which are arranged or formed on the coupling base body 52 on the one hand and on the coupling insert 56 on the other hand. In the connecting position, the connecting elements 110 and 112 are in engagement in a force- and/or positive-locking manner.

The first connecting element 110 is configured in the form of a connecting element recess 114. The second connecting element 112 is configured in the form of a connecting projection 116.

The connecting elements 110 and 112 extend in parallel to an opening plane 118 which is defined by the lateral coupling insert receptacle opening 98 and is also defined by the lateral insertion opening 78.

The connecting element recess 114 of elongated cuboidal configuration is arranged or formed, respectively, pointing in the direction toward the lower coupling insert receptacle opening 100.

Furthermore, the lower coupling insert receptacle opening 100 is open pointing in a direction which is opposed to the direction defined by the first coupling element 60.

The hip joint endoprosthesis system 10 may further comprise a release instrument 120 for releasing the coupling insert 56 from the coupling insert receptacle 54 of the coupling base body 52. It comprises a release member 122.

A release member opening 124 is formed on the coupling base body 52. A length 126 of the release member 122 is greater than a thickness 128 of the coupling base body 52 in the region of the release member opening 124. The release member opening 124 is arranged or formed, respectively, opposite the lateral coupling insert receptacle opening 98.

The release member 122 is configured in the form of a release pin 130 which projects perpendicularly from an end face 136 running transversely to a shaft longitudinal axis 132 of a shaft 134 of the release instrument 120.

A proximal end of the release instrument 120 forms a handle 138.

The release member 122 is preferably provided with an external thread, the release member opening 124 with an internal thread corresponding to the external thread.

By screwing the release pin 130 into the release member opening 124, the coupling insert 56 is pushed out of the coupling insert receptacle 54 in a direction defined by the arrow 140, which is directed counter to the insertion direction 80. Under certain circumstances, large forces may be necessary for this, because the coupling insert 56 must be compressed somewhat in the region of the rib-shaped connecting projection 116, such that the latter can come out of the connecting element recess 114.

In order to facilitate the ejection of the coupling insert 56 out of the coupling insert receptacle 54, a depression 142 is provided commencing from the lateral coupling insert opening 98 on the coupling insert receptacle 54 up to just before the connecting element recess 114, into which depression 142 the connecting projection 116 is able to dip. The later thus only has to overcome a short projecting rib 144, namely both when pushing the coupling insert 56 into the coupling insert receptacle 54 and when pressing the coupling insert 56 out of the coupling insert receptacle 54 with the release instrument 120.

The extraction adapter 46 is preferably configured in such a way that only the edges 86 and 88 of the coupling insert 56 are able to come into contact with the coupling cone 38, but not any edges of the coupling base body 52. It may thus be prevented that the coupling cone 38 may be damaged by the coupling base body 52, which is preferably also formed of a metal.

The first coupling element 60 may in particular be configured identically to a corresponding coupling element on a rasp body which is coupleable to the instrument handle 18 in order to prepare the cavity on the femur bone for the insertion of the prosthesis stem 14.

The hip joint endoprosthesis system described enables a careful extraction of a prosthesis stem 14 from a femur bone, namely without damaging the coupling cone 38.

REFERENCE NUMERAL LIST 10 hip joint endoprosthesis system
12 instrument
14 prosthesis stem
16 hip joint endoprosthesis
18 instrument handle
20 rasp handle
22 striking body
24 striking face
26 instrument body
28 end
30 shaft body
32 end
34 end
36 end face
38 coupling cone
40 end face
42 end
44 neck section
46 extraction adapter
48 coupling body
50 coupling recess
52 coupling base body
54 coupling insert receptacle
56 coupling insert
58 end face
60 first coupling element
62 coupling projection
64 coupling projection longitudinal axis
66 recess
68 second coupling element
70 coupling element receptacle
72 securing member
74 pivot axis
76 locking nose
78 lateral insertion opening
80 arrow
82 longitudinal axis
84 lower insertion opening
86 edge
88 edge
90 inner contour
92 inner cone
94 longitudinal cone axis
96 cross-sectional narrowing
89 lateral coupling insert receptacle opening
100 lower coupling insert receptacle opening
102 undercut
104 annular face
106 connecting device
108 latching or snapping connecting device
110 first connecting element
112 second connecting element
114 connecting element recess
116 connecting projection
118 opening plane
120 release instrument
122 release member
124 release member opening
126 length
128 thickness
130 release pin
132 shaft longitudinal axis
134 shaft
136 end face
138 handle
140 arrow
142 depression
144 rib

What is claimed is:

1. A hip joint endoprosthesis system, comprising:
a medical instrument for extracting an implanted prosthesis stem of a hip joint endoprosthesis from a femur bone of a patient, the medical instrument comprising:
a coupling body with a coupling recess for accommodating a coupling cone protruding from the prosthesis stem,
wherein:
the coupling body comprises a coupling base body and a coupling insert which is accommodated in a coupling insert receptacle of the coupling base body and defines the coupling recess; and
the coupling recess has a lateral insertion opening for inserting the coupling cone into the coupling recess in an insertion direction which runs transversely to a longitudinal axis defined by the coupling cone,
wherein the coupling base body is formed of a harder material than the coupling insert.

2. The hip joint endoprosthesis system in accordance with claim 1, wherein at least one of:
a) the coupling base body is formed of a metal; or
the coupling base body is formed of a metal, namely of an instrument steel; and
b) the coupling insert is formed of a plastic; or
the coupling insert is formed of a plastic, namely at least one of polyetheretherketone (PEEK) and polypropylene (PP) and polyphenylene sulfone (PPSU); and
c) the medical instrument comprises at least one first coupling element for coupling to an instrument handle; or
the medical instrument comprises at least one first coupling element for coupling to an instrument handle, and wherein the first coupling element is configured in the form of a coupling projection.

3. The hip joint endoprosthesis system in accordance with claim 1, wherein:
a) the medical instrument comprises an instrument handle; or
b) the medical instrument comprises an instrument handle which is configured in the form of a rasp handle; or c) the medical instrument comprises an instrument handle, wherein the instrument handle comprises a striking body with a striking face, and wherein the striking body is arranged or formed on a proximal end of the instrument handle or forms the proximal end of the instrument handle; or d) the medical instrument comprises an instrument handle which is configured in the form of a rasp handle, wherein the instrument handle comprises a striking body with a striking face, and wherein the striking body is arranged or formed on a proximal end of the instrument handle or forms the proximal end of the instrument handle.

4. The hip joint endoprosthesis system in accordance with claim 3, wherein:
   a) the instrument handle comprises at least one second coupling element for bringing the instrument handle into engagement in at least one of a force-locking and positive-locking manner with at least one first coupling element of the medical instrument in a coupling position; or
   b) the instrument handle comprises at least one second coupling element for bringing the instrument handle into engagement in at least one of a force-locking and positive-locking manner with at least one first coupling element of the medical instrument in a coupling position, wherein at least one of:
      b1) the at least one second coupling element is configured in the form of a coupling element receptacle for accommodating the at least one first coupling element; and
      b2) the at least one second coupling element is arranged or formed on a distal end of the instrument handle or forms the distal end of the instrument handle.

5. The hip joint endoprosthesis system in accordance with claim 1, wherein the coupling recess is configured to accommodate the coupling cone in at least one of a force-locking and positive-locking manner.

6. The hip joint endoprosthesis system in accordance with claim 1, wherein the insertion direction runs perpendicularly to the longitudinal axis defined by the coupling cone.

7. The hip joint endoprosthesis system in accordance with claim 6, wherein at least one of:
   a) the coupling recess has a lower insertion opening which is open in a direction transverse to the insertion opening; or
   the coupling recess has a lower insertion opening which is open in a direction perpendicular to the insertion opening; or
   the coupling recess has a lower insertion opening which is open in a direction transverse to the insertion opening, and wherein the coupling base body surrounds the coupling insert in such a way that the lateral insertion opening and the lower insertion opening are freely accessible when the coupling insert is inserted into the coupling insert receptacle; or
   the coupling recess has a lower insertion opening which is open in a direction perpendicular to the insertion opening, and wherein the coupling base body surrounds the coupling insert in such a way that the lateral insertion opening and the lower insertion opening are freely accessible when the coupling insert is inserted into the coupling insert receptacle; and
   b) the coupling insert defines edges or transition regions delimiting at least one of the lateral insertion opening and the lower insertion opening.

8. The hip joint endoprosthesis system in accordance with claim 1, wherein:
   a) the coupling recess has an inner contour which has the form of an inner cone at least in sections; or
   b) the coupling recess has an inner contour which has the form of an inner cone at least in sections, wherein at least one of:
      b1) the inner cone defines a longitudinal cone axis which passes through the lower insertion opening; and
      b2) a cross section of the inner cone increases in the direction toward the lower insertion opening; and
      b3) a cross-sectional narrowing is formed between the inner cone and the lower insertion opening.

9. The hip joint endoprosthesis system in accordance with claim 1, wherein the coupling insert receptacle has a lateral coupling insert receptacle opening and a lower coupling insert receptacle opening.

10. The hip joint endoprosthesis system in accordance with claim 9, wherein at least one of:
    a) the lateral coupling insert receptacle opening is configured for the insertion of the coupling insert into the coupling insert receptacle; and
    b) the coupling insert receptacle has an undercut which is formed by a reduction of a free cross section of the coupling insert receptacle in the direction toward the lower coupling insert receptacle opening; and
    c) the first coupling element is arranged on the coupling base body in such a way that it points counter to or substantially counter to the lower coupling insert receptacle opening.

11. The hip joint endoprosthesis system in accordance with claim 1, wherein the coupling insert is held in the coupling insert receptacle in at least one of a force-locking and positive-locking manner.

12. The hip joint endoprosthesis system in accordance with claim 1, wherein the medical instrument comprises a connecting device for connecting the coupling insert and the coupling base body in a connecting position in at least one of a force-locking and positive-locking manner.

13. The hip joint endoprosthesis system in accordance with claim 12, wherein the connecting device is configured in the form of a latching or snapping connecting device.

14. The hip joint endoprosthesis system in accordance with claim 12, wherein the connecting device comprises first and second connecting elements which are formed on the coupling insert on the one hand and on the coupling base body on the other hand, and wherein the first and second connecting elements are in engagement in at least one of a force-locking and positive-locking manner in the connecting position.

15. The hip joint endoprosthesis system in accordance with claim 14, wherein at least one of:
    a) the first connecting element is configured in the form of a connecting element recess, and wherein the second connecting element is configured in the form of a connecting projection; and
    b) at least one of the first connecting element and the second connecting element extend in parallel or substantially in parallel at least one of to the lateral coupling insert receptacle opening and to the lateral insertion opening; and
    c) the connecting element formed on the coupling base body in the coupling insert receptacle is arranged or formed pointing in the direction toward the lower coupling insert receptacle opening.

16. The hip joint endoprosthesis system in accordance with claim 1, wherein the hip joint endoprosthesis system comprises a release instrument for releasing the coupling insert from the coupling insert receptacle of the coupling base body.

17. The hip joint endoprosthesis system in accordance with claim 16, wherein the release instrument comprises a release member, wherein the coupling base body comprises a release member opening, and wherein the release member has a length which is greater than a thickness of the coupling base body in the region of the release member opening.

18. The hip joint endoprosthesis system in accordance with claim 1, wherein the hip joint endoprosthesis system comprises a release instrument for releasing the coupling insert from the coupling insert receptacle of the coupling base body, wherein the release instrument comprises a release member, wherein the coupling base body comprises a release member opening, and wherein the release member has a length which is greater than a thickness of the coupling base body in the region of the release member opening, and wherein at least one of:
 a) the release member opening is arranged or formed opposite the lateral coupling insert receptacle opening; and
 b) the release member is configured in the form of a release pin projecting from the release instrument; and
 c) the release member is provided with an external thread, and wherein the release member opening is provided with an internal thread corresponding to the external thread.

19. The hip joint endoprosthesis system in accordance with claim 1, wherein the hip joint endoprosthesis system comprises a prosthesis stem of a hip joint endoprosthesis, which prosthesis stem has a projecting coupling cone.

20. A hip joint endoprosthesis system, comprising:
 a medical instrument for extracting an implanted prosthesis stem of a hip joint endoprosthesis from a femur bone of a patient, the medical instrument comprising:
  a coupling body with a coupling recess for accommodating a coupling cone protruding from the prosthesis stem, the coupling body comprising a coupling base body and a coupling insert which is accommodated in a coupling insert receptacle of the coupling base body and defines the coupling recess, and
  a connecting device for connecting the coupling insert and the coupling base body in a connecting position in at least one of a force-locking and positive-locking manner,
 wherein the connecting device is configured in the form of a latching or snapping connecting device.

21. The hip joint endoprosthesis system in accordance with claim 20, wherein the coupling base body is formed of a harder material than the coupling insert.

22. The hip joint endoprosthesis system in accordance with claim 20, wherein the connecting device comprises first and second connecting elements which are formed on the coupling insert on the one hand and on the coupling base body on the other hand, and wherein the first and second connecting elements are in engagement in at least one of a force-locking and positive-locking manner in the connecting position.

23. The hip joint endoprosthesis system in accordance with claim 22, wherein at least one of:
 a) the first connecting element is configured in the form of a connecting element recess, and wherein the second connecting element is configured in the form of a connecting projection; and
 b) at least one of the first connecting element and the second connecting element extend in parallel or substantially in parallel at least one of to the lateral coupling insert receptacle opening and to the lateral insertion opening; and
 c) the connecting element formed on the coupling base body in the coupling insert receptacle is arranged or formed pointing in the direction toward the lower coupling insert receptacle opening.

24. The hip joint endoprosthesis system in accordance with claim 20, wherein the hip joint endoprosthesis system comprises a release instrument for releasing the coupling insert from the coupling insert receptacle of the coupling base body, wherein the release instrument comprises a release member, wherein the coupling base body comprises a release member opening, and wherein the release member has a length which is greater than a thickness of the coupling base body in the region of the release member opening, and wherein at least one of:
 a) the release member opening is arranged or formed opposite the lateral coupling insert receptacle opening; and
 b) the release member is configured in the form of a release pin projecting from the release instrument; and
 c) the release member is provided with an external thread, and wherein the release member opening is provided with an internal thread corresponding to the external thread.

25. The hip joint endoprosthesis system in accordance with claim 20, wherein the hip joint endoprosthesis system comprises a prosthesis stem of a hip joint endoprosthesis, which prosthesis stem has a projecting coupling cone.

26. A hip joint endoprosthesis system, comprising:
 a medical instrument for extracting an implanted prosthesis stem of a hip joint endoprosthesis from a femur bone of a patient, the medical instrument comprising:
  a coupling body with a coupling recess for accommodating a coupling cone protruding from the prosthesis stem,
 wherein:
 the coupling body comprises a coupling base body and a coupling insert which is accommodated in a coupling insert receptacle of the coupling base body and defines the coupling recess,
 the coupling insert receptacle has a lateral coupling insert receptacle opening and a lower coupling insert receptacle opening, and
 the lateral coupling insert receptacle opening is configured for the insertion of the coupling insert into the coupling insert receptacle.

27. The hip joint endoprosthesis system in accordance with claim 26, wherein at least one of:
 a) the coupling insert receptacle has an undercut which is formed by a reduction of a free cross section of the coupling insert receptacle in the direction toward the lower coupling insert receptacle opening; and
 b) the first coupling element is arranged on the coupling base body in such a way that it points counter to or substantially counter to the lower coupling insert receptacle opening.

28. The hip joint endoprosthesis system in accordance with claim 26, wherein:
 a) the coupling recess has an inner contour which has the form of an inner cone at least in sections; or
 b) the coupling recess has an inner contour which has the form of an inner cone at least in sections, wherein at least one of:

b1) the inner cone defines a longitudinal cone axis which passes through the lower insertion opening; and b2) a cross section of the inner cone increases in the direction toward the lower insertion opening; and b3) a cross-sectional narrowing is formed between the inner cone and the lower insertion opening.

29. The hip joint endoprosthesis system in accordance with claim 26, wherein the hip joint endoprosthesis system comprises a release instrument for releasing the coupling insert from the coupling insert receptacle of the coupling base body, wherein the release instrument comprises a release member, wherein the coupling base body comprises a release member opening, and wherein the release member has a length which is greater than a thickness of the coupling base body in the region of the release member opening, and wherein at least one of:
  a) the release member opening is arranged or formed opposite the lateral coupling insert receptacle opening; and
  b) the release member is configured in the form of a release pin projecting from the release instrument; and
  c) the release member is provided with an external thread, and wherein the release member opening is provided with an internal thread corresponding to the external thread.

30. The hip joint endoprosthesis system in accordance with claim 26, wherein the hip joint endoprosthesis system comprises a prosthesis stem of a hip joint endoprosthesis, which prosthesis stem has a projecting coupling cone.

* * * * *